(12) United States Patent
Lareau et al.

(10) Patent No.: US 8,894,629 B2
(45) Date of Patent: Nov. 25, 2014

(54) HIGH FLOW CATHETER VALVE

(75) Inventors: Raymond J. Lareau, Westford, MA (US); Benjamin D. Bell, Shrewsbury, MA (US)

(73) Assignee: Navilyst Medical, Inc., Marlborough, MA (US)

( * ) Notice: Subject to any disclaimer, the term of this patent is extended or adjusted under 35 U.S.C. 154(b) by 284 days.

(21) Appl. No.: 13/275,894

(22) Filed: Oct. 18, 2011

(65) Prior Publication Data

US 2013/0096514 A1    Apr. 18, 2013

(51) Int. Cl.
*A61M 25/16* (2006.01)
*A61M 5/00* (2006.01)
*A61M 39/00* (2006.01)
*A61M 25/00* (2006.01)
*A61M 39/24* (2006.01)

(52) U.S. Cl.
CPC ....... *A61M 39/24* (2013.01); *A61M 2039/2426* (2013.01)
USPC ........... 604/537; 604/246; 604/533; 604/284; 604/247

(58) Field of Classification Search
CPC ............ A61M 2039/2426; A61M 2039/2433; A61M 39/24; A61M 39/00; A61M 39/22; A61M 39/10; A61M 39/26; A61M 2025/0076; A61M 2039/1083; A61M 2039/1088; A61M 39/105
USPC ......... 604/264, 533–534, 537, 246–249, 284, 604/535, 536
See application file for complete search history.

(56) References Cited

U.S. PATENT DOCUMENTS

| | | | |
|---|---|---|---|
| 4,232,677 A * | 11/1980 | Leibinsohn | 604/247 |
| 2001/0021830 A1* | 9/2001 | Yamada et al. | 604/249 |
| 2009/0076485 A1* | 3/2009 | Mubarak | 604/533 |

* cited by examiner

*Primary Examiner* — Bhisma Mehta
*Assistant Examiner* — Bradley G Thomas, Jr.
(74) *Attorney, Agent, or Firm* — Ryan D. Artis

(57) ABSTRACT

Valves for regulating fluid flows through medical devices are provided. In some embodiments, the valves are adapted for use in high flow applications and multiple valve elements disposed across a plurality of fluid flow paths branching from and into one or more inlets and outlets.

9 Claims, 5 Drawing Sheets

HIGH FLOW CATHETER VALVE

TECHNICAL FIELD

The present invention relates to pressure-activated valves for use in high-flow medical applications.

BACKGROUND

Vascular catheters are typically connected to external fluid sources via hubs with, for example, luer connections. When a luer tip is removed from a catheter, a pressure differential is created which sometimes causes blood to reflux into the catheter where it can clot, occluding the catheter or becoming a nidus for infection. In practice, this pressure differential is addressed by the use of external manual clamps—which must be closed by an operator when a connection is withdrawn—or through the use of internal catheter valves, which mechanically isolate the lumen of the catheter from changes in pressure at the hub with limited operator input. Internal valves have the benefit of operating rapidly and reliably to prevent transmission of negative pressure without the risk of operator error.

State of the art valves for vascular applications, such as the PASV® Valve produced by Navilyst Medical, Inc. (Marlborough, Mass.), typically comprise an elastomeric disk that includes one or more slits along an axis of the disk. If the disk is not round (e.g. if it is elliptical), the slit is typically oriented along the major axis of the disk. When a fluid pressure differential of sufficient magnitude arises across the disk, the disk deforms so that the edges of the slit or slits are separated and fluid can flow across the valve. The pressure necessary to deform the disk depends on variables which may include, without limitation, the thickness of the disk and the Young's modulus of the material used.

Although the disk may be able to deform very rapidly, some latency may inevitably exist between a change in the pressure across the valve and the time that flow across the valve reaches a steady state. It is preferable to minimize the response time of the disk in order to minimize the potential for reflux. Additionally, when the pressure differential across the valve drops below the threshold magnitude and the valve returns to its relaxed state, it should seal completely to avoid leakage through the valve. There is a constant need to improve valve durability and minimize the risk of leakage.

The needs described above are magnified in high-flow or "power injection" applications, such as infusions of contrast agent for contrast-enhanced CT scanning. All valves are subjected to pressure and resist flow to some degree, but valves used for high flow applications are larger and have greater surface areas, and are thereby subjected to greater pressures than other valves, making the issues described above particularly acute. Additionally, valves that are configured for low pressure uses may fail when exposed to the high flows and pressures required for contrast agent infusions. There is a constant need for valves suitable for power injection with improved response and sealing characteristics.

BRIEF DESCRIPTION OF THE INVENTION

The needs described above are addressed by the present invention which provides, in one aspect, a valve suitable for use in power injection applications that separates fluid flow into a plurality of fluid paths, wherein fluid flow is governed by valve elements disposed within the flow paths. The valve elements used in the invention are smaller than valve elements required in valves designed to handle the same pressures and volumes in a single flow path. These smaller valve elements have improved overall response times and re-sealing characteristics relative to larger valve elements. In preferred embodiments, the valve elements are slitted disks and, in certain embodiments, the slit lengths and other dimensions of the disks are chosen to optimize their response times and re-sealing characteristics.

In another aspect, the invention relates to systems for high flow medical applications including valves in which flow is channeled through a plurality of flow paths over a plurality of valve elements in parallel, resulting in more rapid response times and improved sealing characteristics compared to valves having a single larger valve element.

In yet another aspect, the invention relates to methods of making valves of the present invention.

DESCRIPTION OF THE DRAWINGS

The figures provided herein are not necessarily drawn to scale, with emphasis being placed on illustration of the principles of the invention.

DETAILED DESCRIPTION

Figure 1:
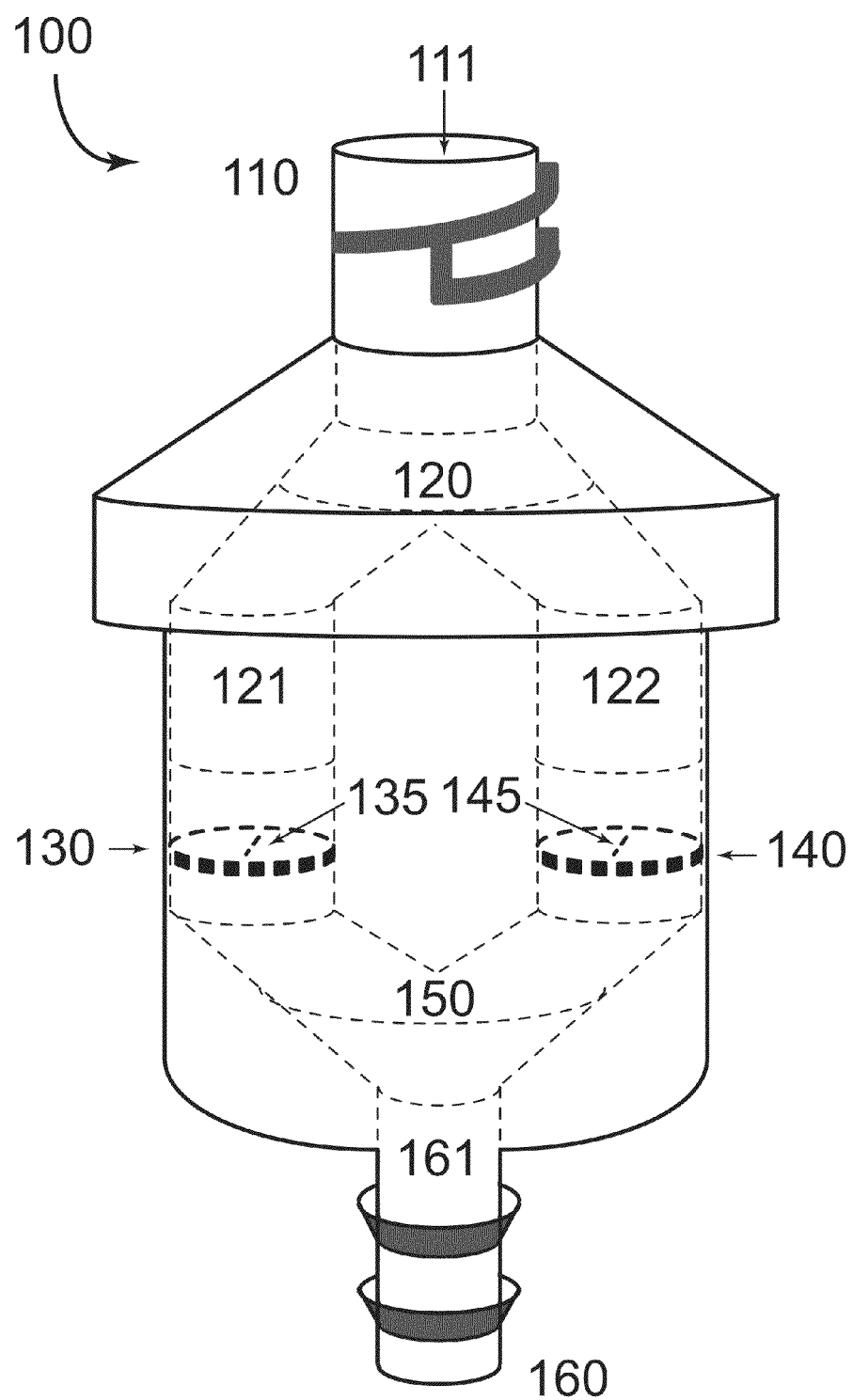
FIG. 1 is a schematic view of a valve according to an embodiment of the present invention.

With reference to the embodiments depicted in FIGS. 1-5, valve 100 has an inlet 110 and an outlet 160 at its proximal and distal ends, respectively. The inlet 110 is preferably configured to connect to a fluid source through a suitable connection means. While FIGS. 1-5 depict inlets having female luer connectors, any other suitable connection means can be used including barbed connectors, male luer connectors, etc. Luer connectors used with the invention may be threaded or non-threaded. The inlet 110 defines an inlet lumen 111 that opens to a proximal branching lumen 120 that is, in turn, open at its distal end to a plurality of intermediate lumens, 121, 122, 123. The intermediate lumens are open at their distal ends to a distal branching lumen 150, which funnels fluid exiting the intermediate lumens into the outlet lumen 161 within the outlet 160 at the distal end of the valve. The outlet 160 is configured to connect to a fluid delivery device such as a catheter (not shown) using any suitable connection known in the art. The figures depict outlet 160 having a barb connector; other suitable connectors may include male or female luer ends, etc.

Disposed within each intermediate lumen 121, 122, 123 is a valve element 130, 140, 170. In a preferred embodiment, each valve element is a flexible elastic disk having one or more slits therethrough, as is known in the art. A non-limiting example of a valve with a flexible elastic disk valve element is disclosed in U.S. Pat. No. 5,843,044 to Moorehead entitled "Outdwelling slit valve and variable control for controlling opening and closing of the slit," the entire disclosure of which is incorporated by reference into the present application. However, any valve design known in the art may be used, including three-dimensional structures such as those disclosed in United States Publication No. 2010/0191192 by Prasad et al. entitled "Three-way Valve for Power Injection in Vascular Access Devices," the entire disclosure of which is incorporated by reference into the present application. In the embodiment of FIG. 1, each valve element 130, 140 has a single slit 135, 145 therethrough. However, any suitable number of slits may be used, and the slits may be arranged in any manner known in the art, including, without limitation, in the arrangements disclosed in United States Publication No. 2005/0171488 by Weaver et al. entitled "Pressure activated safety valve with high flow slit," and in United States Publication No. 2009/0177187 by Weaver et al. entitled "Pressure Activated Valve with Angled Slit." The entire disclosure of both publications is incorporated by reference into the present application. As non limiting examples, valves of the invention can include a single slit or a plurality of slits; the slits can be straight or curved, and can be cut perpendicular to or at an angle to the surface of the disk. The invention includes embodiments utilizing a plurality of slits where the slits run parallel, perpendicular, and at other angles. The slits may intersect, for example to form H-shapes or star shapes, or may not intersect. The slits may be S-shaped, or may combine to form an S-shape.

Though not wishing to be bound by theory, it is believed that the use of a plurality of smaller valve elements and fluid flow paths improves response times and sealing characteristics relative to the use of a larger single valve element by decreasing the distances by which the valve elements must be displaced in order to reach a steady state, and by decreasing the contact areas which must reseal within each valve. For example, in a valve having two parallel slit valve elements, each valve element will incorporate a single slit having a shorter length than a slit in a comparable valve incorporating a single larger valve element with a single slit. In the valve with a plurality of valve elements, each smaller slit will, in absolute terms, be displaced by a smaller distance when fully open than the single slit in the larger valve element, so less time will be required for the smaller slits to respond to a change in pressure. When resealing, the smaller contact area of a slit in a smaller valve element is more likely to reseal completely than a larger slit in a larger valve element.

Additionally, it is believed that, when a plurality of smaller valve elements are used, if one valve element fails, the magnitude of a leak will be substantially less than that of a leak resulting from failure of a large valve element. Moreover, in embodiments where a plurality of valve elements are arranged in parallel, the transient failure of one valve element may promote improved sealing of the other valve elements by decreasing the pressure differential across the valve elements.

With respect to disk valves, any suitable shape is within the scope of the present invention, including the round or elliptical geometries currently known in the art, as well as other geometries such as a single elastomeric membrane incorporating a plurality of valve elements, each valve element disposed across one of a plurality of lumens, as is disclosed in United States Publication No. 2004/018444 by Daly et al. entitled "Pressure Responsive Slit Valve Assembly for a Plurality of Fluids and Uses Thereof." The entire disclosure of this publication is incorporated by reference into the present application.

Figure 4:
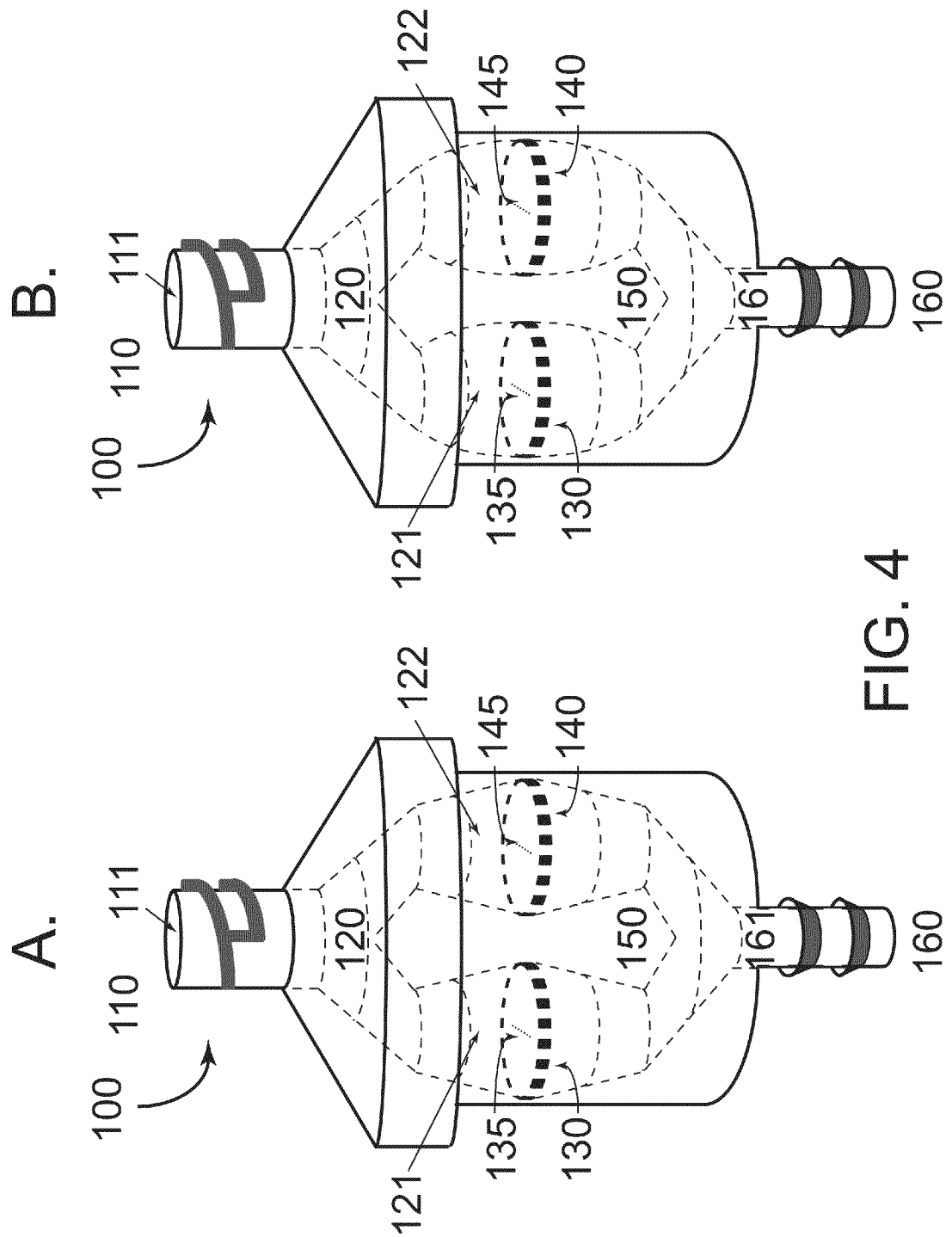
FIG. 4 is a schematic view of a valve according to an embodiment of the present invention.

With respect to lumen geometries, the intermediate lumens may have constant diameters such as shown in FIG. 1, or the lumens may taper as is shown in FIG. 4. The taper of the lumen may be linear, as shown in FIG. 4A, or non-linear, as shown in FIG. 4B. Additionally, the intermediate lumen may taper proximal to the valve element, distal to the valve element, or on both sides thereof.

Figure 3:
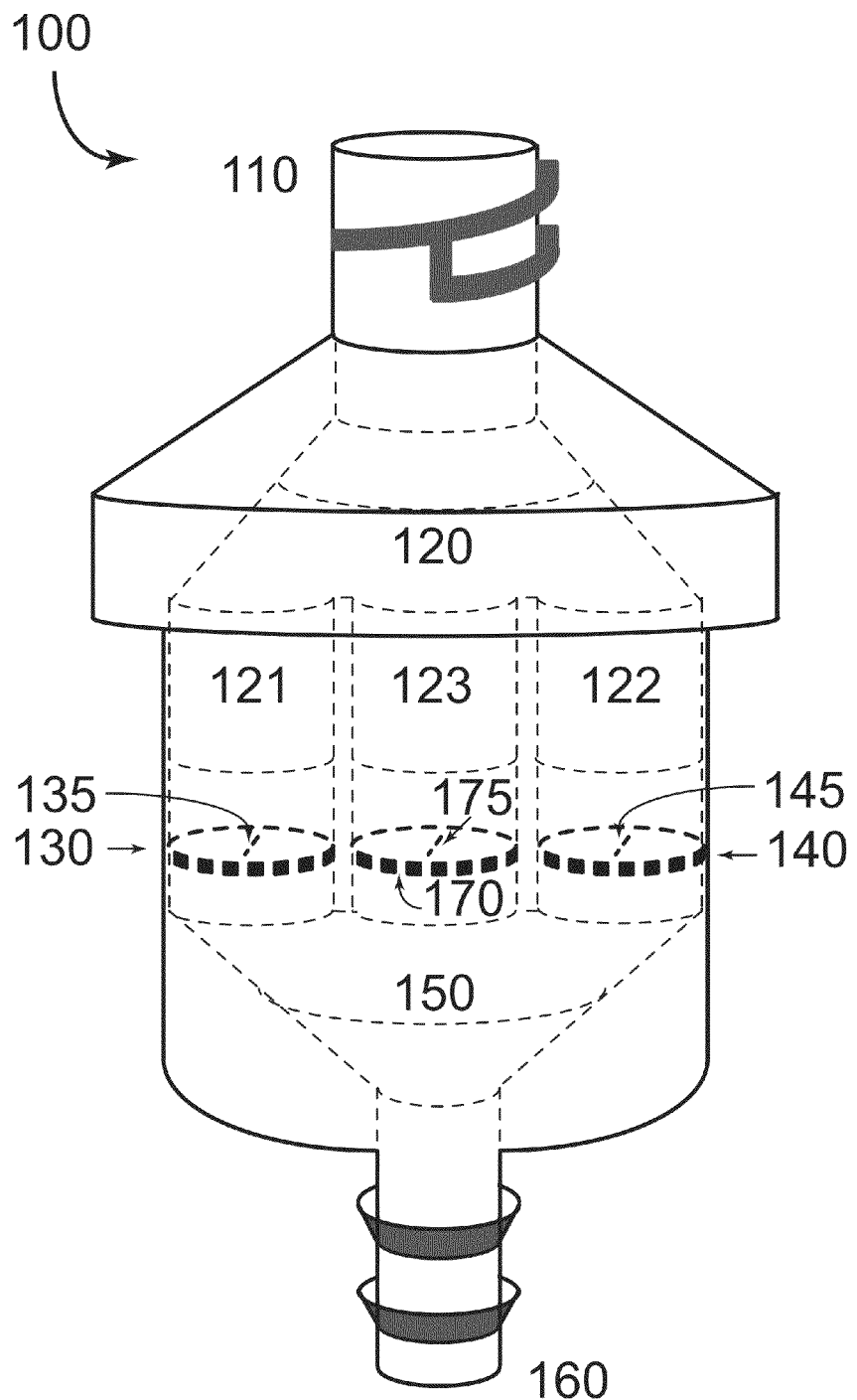
FIG. 3 is a schematic view of a valve according to an embodiment of the present invention.

An embodiment of the present invention with two intermediate lumens is depicted in FIG. 1, but there is no limit to the number of intermediate lumens that may be used. As a non-limiting example, FIG. 3 depicts an embodiment of the present invention with three intermediate lumens, 121, 122, 123, each having a valve element 130, 140, 170 respectively. In the embodiment of FIG. 3, each valve element has a single slit, 135, 145, 175, respectively. Although FIG. 3 depicts the multiple intermediate lumens 121, 122, 123 arranged in parallel, the multiple lumens may be arranged in any suitable way including, as non-limiting examples, in closely packed round, triangular, hexagonal, square or other space saving arrangements, depending on the number of intermediate lumens within the valve.

Figure 2:
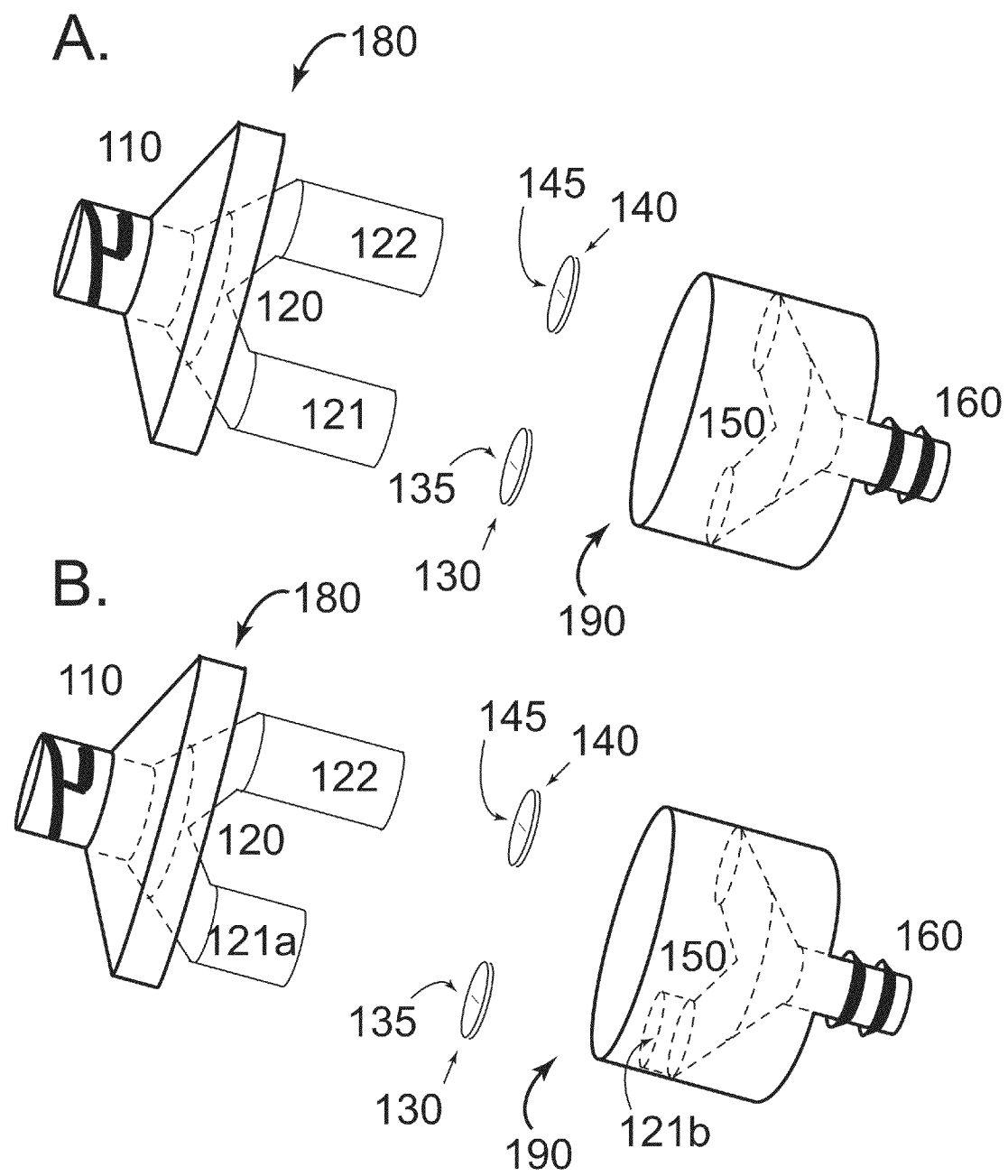
FIG. 2. includes exploded views of valves according to embodiments of the present invention.

In certain embodiments of the present invention such as those depicted in FIG. 2, the valve is assembled by joining a male end 180 to a female end 190. The male and female ends may be joined together using any means known in the art, including press-fitting, sonic welding, heat joining, laser welding, snap fit or through the use of adhesives. In a preferred embodiment, each valve element 130, 140 is held in place in the fully assembled valve between the male housing 180 and the female housing 190. The male housing 180 and the female housing 190 may secure the valve element in the manner disclosed in United States Publication 2011/0009811 by Miller entitled "Method to Secure an Elastic Component in a Valve," or in the manner disclosed in United States Publication No. 2009/0292252 by Lareau et al. entitled "Pressure Activated Valve for High Flow Rate and Pressure Venous Access Applications." The entire disclosure of both publications is incorporated by reference in the present application. The valve elements may also be secured by any other suitable means known in the art.

Though they are depicted in similar positions in many of the drawings, the valve elements 130, 140, 170 may be disposed anywhere within the intermediate lumens 121, 122, 123. In some embodiments, such as that shown in FIG. 2B the valve elements may be positioned at different points along the proximal-distal axis of the valve from one another, so that they are "staggered." In the arrangement shown in FIG. 2B, lumen 121 has been divided into a proximal aspect 121a and a distal aspect 121b, and the valve element 130 resides at the junction between the two aspects of lumen 121 when the valve is fully assembled. Staggered arrangements such as this may be particularly useful to ensure the correct fit of male and female ends 180, 190 during manufacturing.

Figure 5:
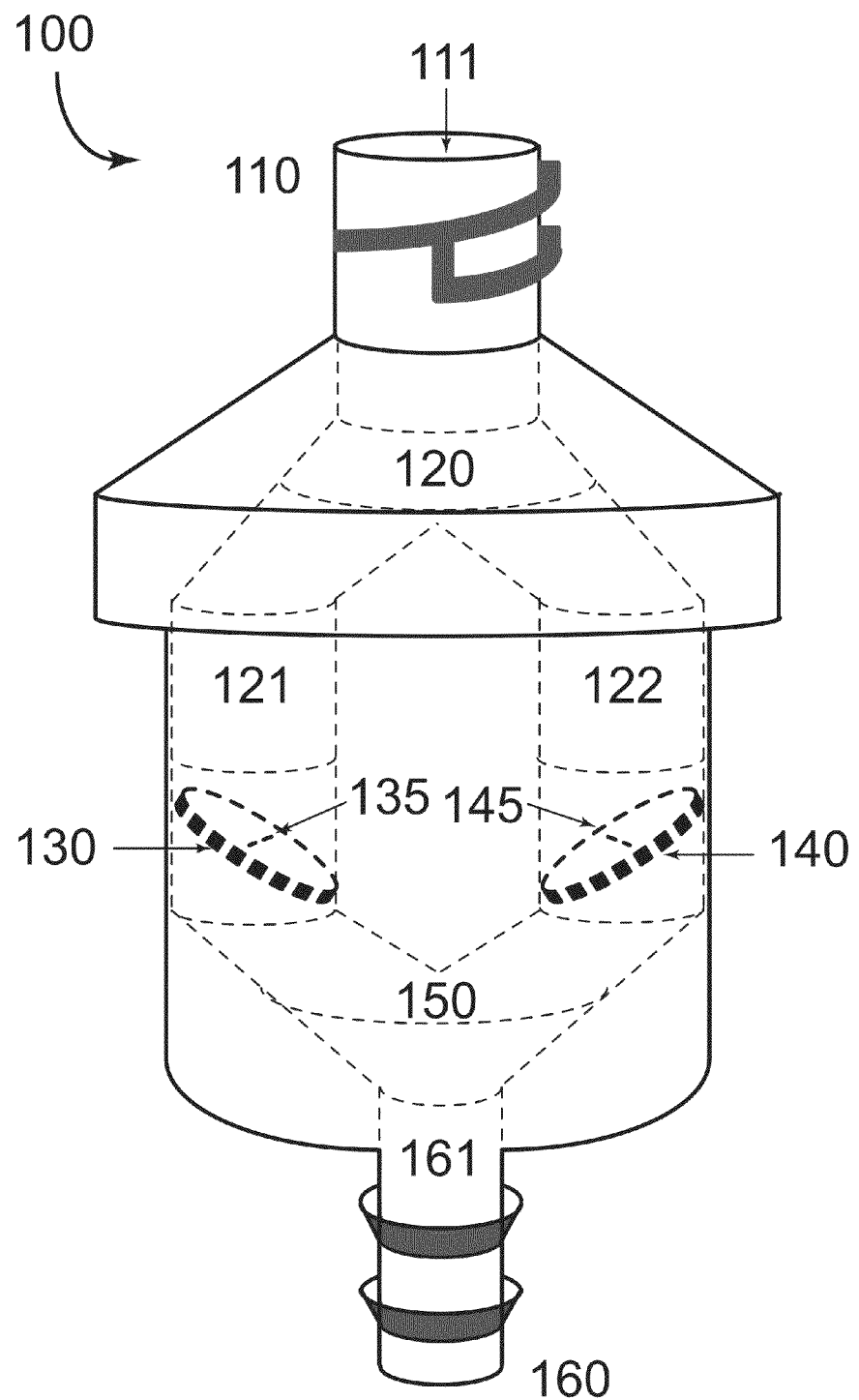
FIG. 5 is a schematic view of a valve according to an embodiment of the present invention.

In certain embodiments, such as that shown in FIG. 5, the valve elements 130, 140 may be angled relative to the central axes of intermediate lumens 121, 122. Angling the valve elements may save space by allowing a valve element with a relatively large diameter to be positioned in a manner that reduces the projected area of the valve element in one or more directions and thereby reducing the overall valve profile.

In preferred embodiments, intermediate lumens 121, 122 have equal cross-sectional areas, and permit equal flows therethrough. However, in alternative embodiments, intermediate lumens 121, 122 have different diameters or different lengths and permit different flows therethrough. As a non-limiting example, in certain embodiments, one intermediate lumen may have a relatively large diameter and may accommodate substantially more fluid flow than another intermediate lumen.

While various aspects and embodiments of the present invention have been described above, it should be understood that they have been presented by way of illustration rather than limitation. The breadth and scope of the present invention is intended to cover all modifications and variations that come within the scope of the following claims and their equivalents.

We claim:

1. A medical device, comprising: a valve housing extending from a proximal end adapted for coupling to a fluid source to a distal end adapted for coupling to a fluid delivery device, the valve housing comprising: a first branching portion having a single proximal fluid channel at a proximal aspect, the single proximal fluid channel being divided into a plurality of intermediate fluid channels at a distal aspect of the first branching portion; a second branching portion having the plurality of intermediate fluid channels at a proximal aspect, the plurality of intermediate fluid channels extending into a plurality of intermediate fluid channels of the second branching portion which then merge into a single distal fluid channel at a distal aspect of the second branching portion; and a plurality of valve elements, each valve element disposed within each of the plurality of intermediate fluid channels; wherein each valve element includes a flexible elastomeric membrane having at least one slit therethrough.

2. The medical device of claim 1, wherein each of the plurality of intermediate fluid channels has a substantially circular cross-section.

3. The medical device of claim 1, wherein each of the plurality of intermediate fluid channels has a substantially elliptical cross-section.

4. The medical device of claim 1, wherein a maximum flow permitted by each intermediate fluid channel is equal.

5. The medical device of claim 1, wherein the at least one slit is curved.

6. The medical device of claim 1, wherein the at least one slit is linear.

7. The medical device of claim 1, wherein each valve element is disposed diagonally across the intermediate fluid channels.

8. The medical device of claim 1, wherein the housing includes male and female valve housing portions, wherein the male and female housing portions define said first and second branching portions and wherein the male and female housing portions are adapted to sealingly engage with one-another.

9. The medical device of claim 8, wherein the valve elements are at least partially sandwiched between securement features on each of said male and female housing portions.

\* \* \* \* \*